(12) United States Patent
Majercak et al.

(10) Patent No.: US 7,918,884 B2
(45) Date of Patent: Apr. 5, 2011

(54) STENT FOR TREATMENT OF BIFURCATED LESIONS

(75) Inventors: David C. Majercak, Stewartsville, NJ (US); Matthew Krever, Warren, NJ (US); Jin S. Park, Parsippany, NJ (US); Robert S. Burgermeister, Bridgewater, NJ (US); Hikmat Hojeibane, Princeton, NJ (US); Martin B. Leon, New York, NY (US)

(73) Assignee: Cordis Corporation, Bridgewater, NJ (US)

( * ) Notice: Subject to any disclaimer, the term of this patent is extended or adjusted under 35 U.S.C. 154(b) by 1260 days.

(21) Appl. No.: 10/863,192

(22) Filed: Jun. 8, 2004

(65) Prior Publication Data
US 2005/0288771 A1 Dec. 29, 2005

Related U.S. Application Data

(63) Continuation-in-part of application No. 10/373,489, filed on Feb. 25, 2003.

(51) Int. Cl.
*A61F 2/01* (2006.01)
(52) U.S. Cl. .................................................... 623/1.15
(58) Field of Classification Search .................. 623/1.12, 623/1.15, 1.35, 1.16; 606/108, 194
See application file for complete search history.

(56) References Cited

U.S. PATENT DOCUMENTS

| | | | |
|---|---|---|---|
| 5,192,307 A | 3/1993 | Wall | |
| 5,354,308 A | 10/1994 | Simon et al. | |
| 5,397,355 A | 3/1995 | Marin et al. | |
| 5,733,330 A | 3/1998 | Cox | |
| 5,766,239 A | 6/1998 | Cox | |
| 5,800,526 A | 9/1998 | Anderson et al. | |
| 5,911,732 A | 6/1999 | Hojeibane | |
| 5,938,682 A | 8/1999 | Hojeibane et al. | |

(Continued)

FOREIGN PATENT DOCUMENTS

DE 29701758 U1 3/1997

(Continued)

OTHER PUBLICATIONS

European Search Report No. EP 02253789 dated Jan. 16, 2003.

(Continued)

*Primary Examiner* — Michael J Milano
*Assistant Examiner* — Victor X Nguyen
(74) *Attorney, Agent, or Firm* — Louis J. Capezzuto

(57) ABSTRACT

A stent includes a lattice defining a substantially cylindrical configuration having a proximal end portion and a distal end portion, and a middle portion between the proximal end and the distal end. The lattice being moveable from a crimped state to an expanded state, and a plurality of adjacent hoops. Each hoop has a plurality of adjacent loops. Additionally, the stent further includes a plurality of bridges connecting adjacent hoops and a plurality of extensions on the lattice. Each of the hoops and bridges define a cell. The proximal end portion and the distal end portion of the lattice have at least one cell respectively and the middle portion of the lattice has at least one cell. The plurality of extensions are on the middle portion of the lattice. The plurality of extensions are cantilevered projections from the bridges and/or hoops of the lattice. The plurality of extensions are movably deformable in a direction away from the lattice, for example, at least some of the extensions are movably deformable in a direction away from the bridges and at least some of the extensions are movably deformable in a direction away from the hoops.

20 Claims, 13 Drawing Sheets

U.S. PATENT DOCUMENTS

| | | | |
|---|---|---|---|
| 5,997,563 A | 12/1999 | Kretzers | |
| 6,022,371 A | 2/2000 | Killion | |
| 6,033,436 A | 3/2000 | Steinke et al. | |
| 6,066,167 A | 5/2000 | Lau et al. | |
| 6,083,258 A | 7/2000 | Yadav | |
| 6,129,754 A | 10/2000 | Kanesaka et al. | |
| 6,129,755 A | 10/2000 | Mathis et al. | |
| 6,156,062 A | 12/2000 | McGuinness | |
| 6,171,334 B1 | 1/2001 | Cox | |
| 6,174,316 B1 | 1/2001 | Tuckey et al. | |
| 6,190,403 B1 | 2/2001 | Fischell et al. | |
| 6,210,429 B1 | 4/2001 | Vardi et al. | |
| 6,251,134 B1 | 6/2001 | Alt et al. | |
| 6,258,116 B1 | 7/2001 | Hojeibane | |
| 6,277,078 B1 | 8/2001 | Porat et al. | |
| 6,325,826 B1 * | 12/2001 | Vardi et al. | 623/1.35 |
| 6,346,089 B1 | 2/2002 | Dibie | |
| 6,599,314 B2 | 7/2003 | Mathis | |
| 6,599,316 B2 | 7/2003 | Vardi et al. | |
| 6,673,107 B1 | 1/2004 | Brandt et al. | |
| 6,676,696 B1 | 1/2004 | Marotta et al. | |
| 6,942,681 B2 | 9/2005 | Johnson | |
| 2001/0003161 A1 | 6/2001 | Vardi et al. | |
| 2001/0004706 A1 | 6/2001 | Hojeibane | |
| 2001/0016767 A1 | 8/2001 | Wilson et al. | |
| 2002/0042650 A1 | 4/2002 | Vardi et al. | |
| 2002/0111671 A1 | 8/2002 | Stenzel | |
| 2002/0133183 A1 * | 9/2002 | Lentz et al. | 606/155 |

FOREIGN PATENT DOCUMENTS

| | | |
|---|---|---|
| DE | 19653721 A1 | 4/1998 |
| DE | 19728337 A | 1/1999 |
| DE | 199 50 756 A1 | 2/1999 |
| EP | 1179323 A2 | 2/2002 |
| EP | 1267748 B1 | 1/2003 |
| WO | WO 98/26732 A1 | 6/1998 |
| WO | WO 00/59405 A1 | 10/2000 |
| WO | WO 01/30271 A2 | 5/2001 |
| WO | WO 03/055414 A1 | 7/2003 |
| WO | WO 03/063924 A1 | 8/2003 |
| WO | WO 03/094798 A | 11/2003 |
| WO | WO 2004/032801 A1 | 4/2004 |

OTHER PUBLICATIONS

European Search Report EP05253501 dated Oct. 25, 2005.
European Search Report Application No. 04 250 845.7 dated Apr. 16, 2007.
European Office Action dated Apr. 18, 2007.

* cited by examiner

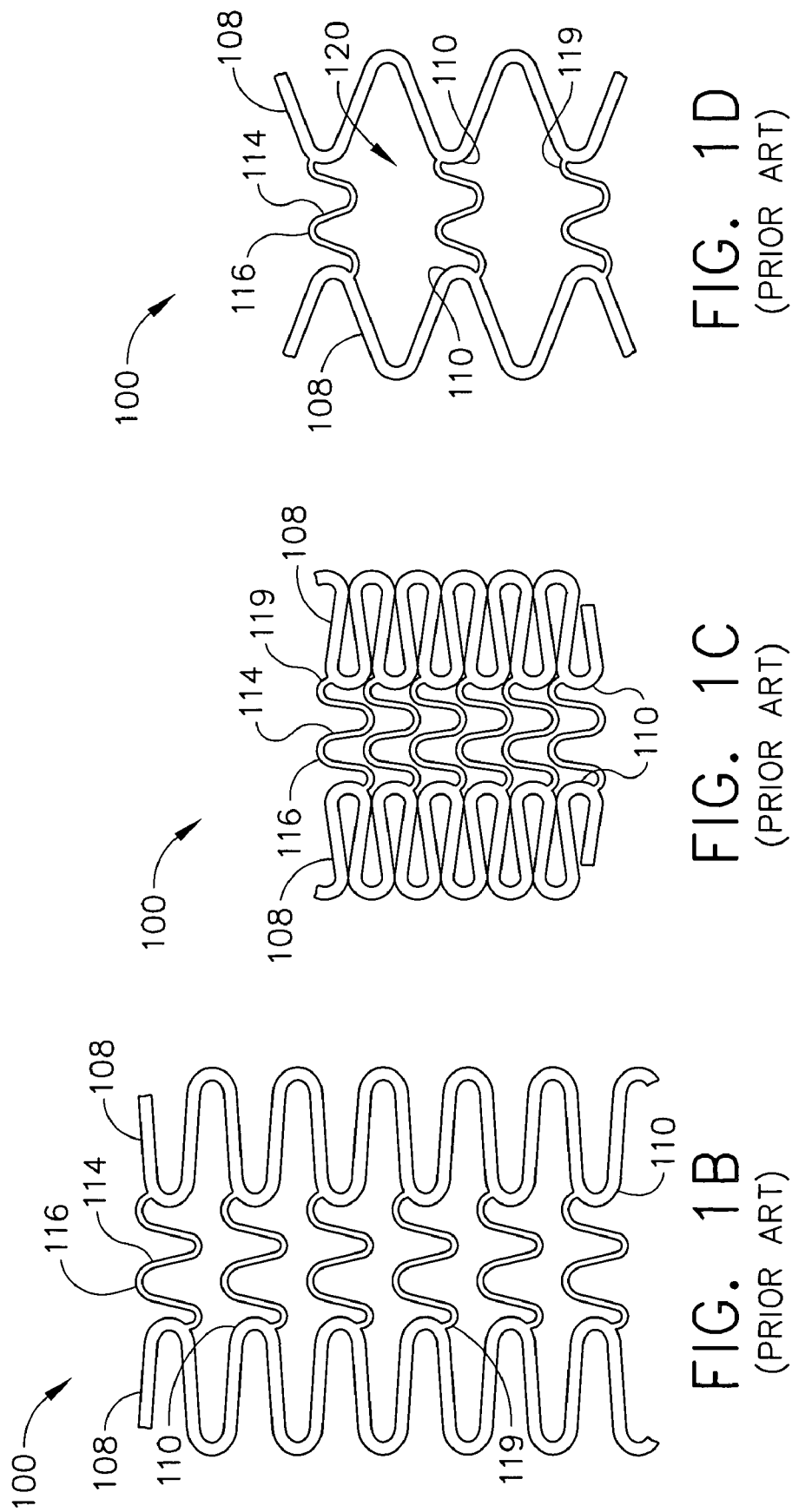

STENT FOR TREATMENT OF BIFURCATED LESIONS

This is a continuation-in-part application of Ser. No. 10/373,489 filed Feb. 25, 2003 which is incorporated herein by reference.

FIELD OF THE INVENTION

The present invention relates, in general, to intralumenal medical devices, and, more particularly, to a new and useful stent having a non-uniform longitudinal pattern whereby the center section of the stent is more open in design than the proximal and distal sections of the stent as well as deformable struts for supporting and conforming to the ostium of a vessel side branch for enhancing vessel coverage and accommodating the side branches of vessels.

BACKGROUND ART

A stent is commonly used as a tubular structure left inside the lumen of a duct to relieve an obstruction. Commonly, stents are inserted into the lumen in a non-expanded form and are then expanded autonomously (or with the aid of a second device) in situ. When used in coronary artery procedures such as an angioplasty procedure for relieving stenosis, stents are placed percutaneously through the femoral artery. In this type of procedure, stents are delivered on a catheter and are either self-expanding or, in the majority of cases, expanded by a balloon. Self-expanding stents do not need a balloon to be deployed. Rather the stents are constructed using metals with spring-like or superelastic properties (i.e., Nitinol), which inherently exhibit constant radial support. Self-expanding stents are also often used in vessels close to the skin (i.e., carotid arteries) or vessels that can experience a lot of movement (i.e., popliteal artery). Due to a natural elastic recoil, self-expanding stents withstand pressure or shifting and maintain their shape.

As mentioned above, the typical method of expansion for balloon expanded stents occurs through the use of a catheter mounted angioplasty balloon, which is inflated within the stenosed vessel or body passageway, in order to shear and disrupt the obstructions associated with the wall components of the vessel and to obtain an enlarged lumen.

Balloon-expandable stents involve crimping the device onto an angioplasty balloon. The stent takes shape as the balloon is inflated and remains in place when the balloon and delivery system are deflated and removed.

In addition, balloon-expandable stents are available either pre-mounted or unmounted. A pre-mounted system has the stent already crimped on a balloon, while an unmounted system gives the physician the option as to what combination of devices (catheters and stents) to use. Accordingly, for these types of procedures, the stent is first introduced into the blood vessel on a balloon catheter. Then, the balloon is inflated causing the stent to expand and press against the vessel wall. After expanding the stent, the balloon is deflated and withdrawn from the vessel together with the catheter. Once the balloon is withdrawn, the stent stays in place permanently, holding the vessel open and improving the flow of blood.

Additionally, the presence of vessel side branches has had a major influence on the strategy of angioplasty for over a decade. It is common thought that over half of angioplasty procedures may place a vessel side branch in danger. The presence of side branches may also increase procedural complications. The occlusion rate of side branches during coronary angioplasty ranges from 3-15%, depending on the clinical and anatomic features of the vessels. Stents may improve or worsen the flow through vessel side branches in both elective and bailout settings. The concept of "stent jail" is described as the incarceration of vessel side branches when their ostia are covered and made inaccessible by trunk vessel stenting.

To date, there have been no adequate stent designs or methods for stenting a bifurcated vessel that can avoid the problem of stent jailing in any appreciable or reportable way. The present invention is directed toward solving this stent jailing problem through a novel stent and novel method of use.

SUMMARY OF THE INVENTION

The present invention relates to a novel stent and novel method of use for treating a bifurcated lesion in a vessel. In one embodiment, a stent in accordance with the present invention comprises a lattice defining a substantially cylindrical configuration having a proximal end portion and a distal end portion, and a middle portion between the proximal end portion and the distal end portion. The lattice is movable from a crimped state to an expanded state. The lattice also has a plurality of adjacent hoops wherein each hoop has a plurality of adjacent loops. A plurality of bridges connect adjacent hoops. Additionally, a plurality of extensions are located on at least some portions of the lattice. Each of the hoops and extensions define a cell. And, the proximal end portion and the distal end portion of the lattice have at least one cell respectively and the middle portion of the lattice has at least one cell containing a plurality of deformable extensions. The at least one cell of the middle portion has spacing between adjacent hoops that is greater than the spacing between adjacent hoops of the proximal end portion and distal end portion respectively.

The plurality of extensions are cantilevered projections from the bridges of the lattice. And, the plurality of extensions are movably deformable in a direction away from the lattice and preferably external to the outer diameter of the stent. Preferably, at least some of the extensions are movably deformable in a direction away from the bridges. And preferably, at least some of the extensions are movably deformable in a direction away from the hoops.

Preferably, the stent in accordance with the present invention has one or more of the extensions that comprise a center arm terminating in a bifurcation.

Additionally or optionally, the one or more of the extensions comprise one or more arms extending from the bifurcation.

More preferably, the one or more of the extensions comprise a first arm and a second arm extending from the bifurcation. In some embodiments according to the present invention, the first arm is at a length shorter than the length of the second arm, or vice versa, i.e. the first arm is at a length longer than the length of the second arm.

Moreover, the stent according to the present invention further comprises a drug on one or more portions of the lattice. In other embodiments according to the present invention, the stent further comprises a drug and polymer combination on one or more portions of the lattice. Particular examples of appropriate drugs include rapamycin, paclitaxel and a number of other drugs addressed later in this disclosure.

Furthermore, the stent according to the present invention is made of various materials. One material for the stent is a metal alloy such as stainless steel. Another material for the stent is a superelastic material which includes a superelastic alloy such as NiTi. Other materials include Cobalt based Alloys such as Cobalt-Chrome (L605).

Another appropriate material for the composition of the stent is a polymeric material. In some embodiments in accordance with the present invention, the stent is made of a biodegradable polymer.

The present invention also is directed to a novel method for treating a bifurcated lesion in a vessel. In one embodiment according to the present invention, a method for treating a bifurcated vessel wherein the bifurcated vessel has a main vessel and a side branch vessel extending from the main vessel comprises the steps of:

identifying a site in the main vessel;

placing a stent at the site in the main vessel, the stent comprising:

a lattice defining a substantially cylindrical configuration having a proximal end portion and a distal end portion, and a middle portion between the proximal end portion and the distal end portion, the lattice being movable from a crimped state to an expanded state, the lattice having a plurality of adjacent hoops, each hoop having a plurality of adjacent loops; a plurality of bridges connecting adjacent hoops; a plurality of extensions on the lattice; each of the hoops and bridges defining a cell; and the proximal end portion and the distal end portion of the lattice having at least one cell respectively and the middle portion of the lattice having at least one cell, the at least one cell of the middle portion having spacing between adjacent hoops that is greater than the spacing between adjacent hoops of the at least one cell of proximal end portion and distal end portion respectively, the lattice containing a plurality of deformable extensions;

dilating the at least one cell of the middle portion adjacent the side branch vessel; and supporting a surface of the side branch vessel with at least one of the plurality of the extensions by deformably moving the at least one of the plurality of extensions away from the lattice and into contact with the surface of the side branch vessel.

In one embodiment according to the present invention, the method further comprises dilating the at least one cell of the middle portion adjacent the side branch vessel with a balloon. In another embodiment according to the present invention, the stent is made of a self-expandable material such as NiTi and the at least one cell of the middle portion is dilated due to shape memory aspects of the at least one cell (adjacent hoops and bridges) and the extensions associated therewith.

In other embodiments in accordance with the present invention, the method further comprises dilating the at least one cell of the middle portion adjacent an ostium of the side branch vessel. The dilating of the at least one cell of the middle portion adjacent an ostium of the side branch vessel can be conducted with a balloon.

The method according to the present invention further comprises placing a second stent in the side branch vessel. Accordingly, the second stent is placed in the side branch vessel at the ostium, and/or the second stent is placed in the side branch vessel adjacent the dilated at least one cell of the middle portion of the first stent, and/or the second stent is placed in the side branch vessel within the dilated at least one cell of the middle portion of the first stent.

Another embodiment in accordance with the present invention is directed to a method for treating a bifurcated vessel wherein the bifurcated vessel has a first vessel and a second vessel extending from the first vessel. The method comprises the steps of:

identifying a site in the first vessel;

placing a stent at the site in the first vessel, the stent comprising:

a lattice defining a substantially cylindrical configuration having a proximal end portion and a distal end portion, and a middle portion between the proximal end portion and the distal end portion, the lattice being movable from a crimped state to an expanded state, the lattice having a plurality of adjacent hoops; a plurality of bridges connecting adjacent hoops; a plurality of extensions on the lattice; each of the hoops and bridges defining a cell; and the proximal end portion and the distal end portion of the lattice having at least one cell respectively and the middle portion of the lattice having at least one cell, containing a plurality of deformable extensions;

dilating the at least one cell of the middle portion adjacent the second vessel; and supporting a surface of the second vessel with at least one of the plurality of the extensions by deformably moving the at least one of the plurality of extensions away from the lattice and into contact with the surface of the second vessel.

BRIEF DESCRIPTION OF THE DRAWINGS

The novel features of the invention are set forth with particularity in the appended claims. The invention itself, however, both as to organization and methods of operation, together with further objects and advantages thereof, may be best understood by reference to the following description, taken in conjunction with the accompanying drawings in which:

FIG. 1B is a partial side view of a section of the prior art stent of FIG. 1A in a configuration conducive for a polishing manufacturing step;

FIG. 1C is a partial side view of a section of the prior art stent of FIG. 1A in the crimped state;

FIG. 1D is a partial side view of a section of the prior art stent of FIG. 1A in an expanded state;

DETAILED DESCRIPTION OF THE INVENTION

As known in the art and best illustrated in FIGS. 1A-1D and 2A-2C, a stent 100,100a respectively is an expandable prosthesis for a body passageway. It should be understood that the terms "stent" and "prosthesis" are interchangeably used to some extent in describing the present invention, insofar as the method, apparatus, and structures of the present invention may be utilized not only in connection with an expandable intraluminal vascular graft for expanding partially occluded segments of a blood vessel, duct or body passageways, such as within an organ, but may so be utilized for many other purposes as an expandable prosthesis for many other types of body passageways. For example, expandable prostheses may also be used for such purposes as: (1) supportive graft placement within blocked arteries opened by transluminal recanalization, but which are likely to collapse in the absence of internal support; (2) similar use following catheter passage through mediastinal and other veins occluded by inoperable cancers; (3) reinforcement of catheter created intrahepatic communications between portal and hepatic veins in patients suffering from portal hypertension; (4) supportive graft placement of narrowing of the esophagus, the intestine, the ureters, the uretha, etc.; (5) intraluminally bypassing a defect such as an aneurysm or blockage within a vessel or organ; and (6) supportive graft reinforcement of reopened and previously obstructed bile ducts. Accordingly, use of the term "prothesis" encompasses the foregoing usages within various types of body passageways, and the use of the term "intraluminal graft" encompasses use for expanding the lumen of a body passageway. Further in this regard, the term "body passageway" encompasses any lumen or duct within the human body, such as those previously described, as well as any vein, artery, or blood vessel within the human vascular system.

As used herein, the terms "biodegradable", "degradable", "degradation", "degraded", "bioerodible", "erodible" or "erosion" are used interchangeably and are defined as the breaking down or the susceptibility of a material or component to break down or be broken into products, byproducts, components or subcomponents over time such as days, weeks, months or years.

As used herein, the terms "bioabsorbable", "absorbable", "resorbable" and "bioresorbable" are used interchangeably and are defined as the biologic elimination of the products of degradation by metabolism and/or excretion.

Figure 1A:
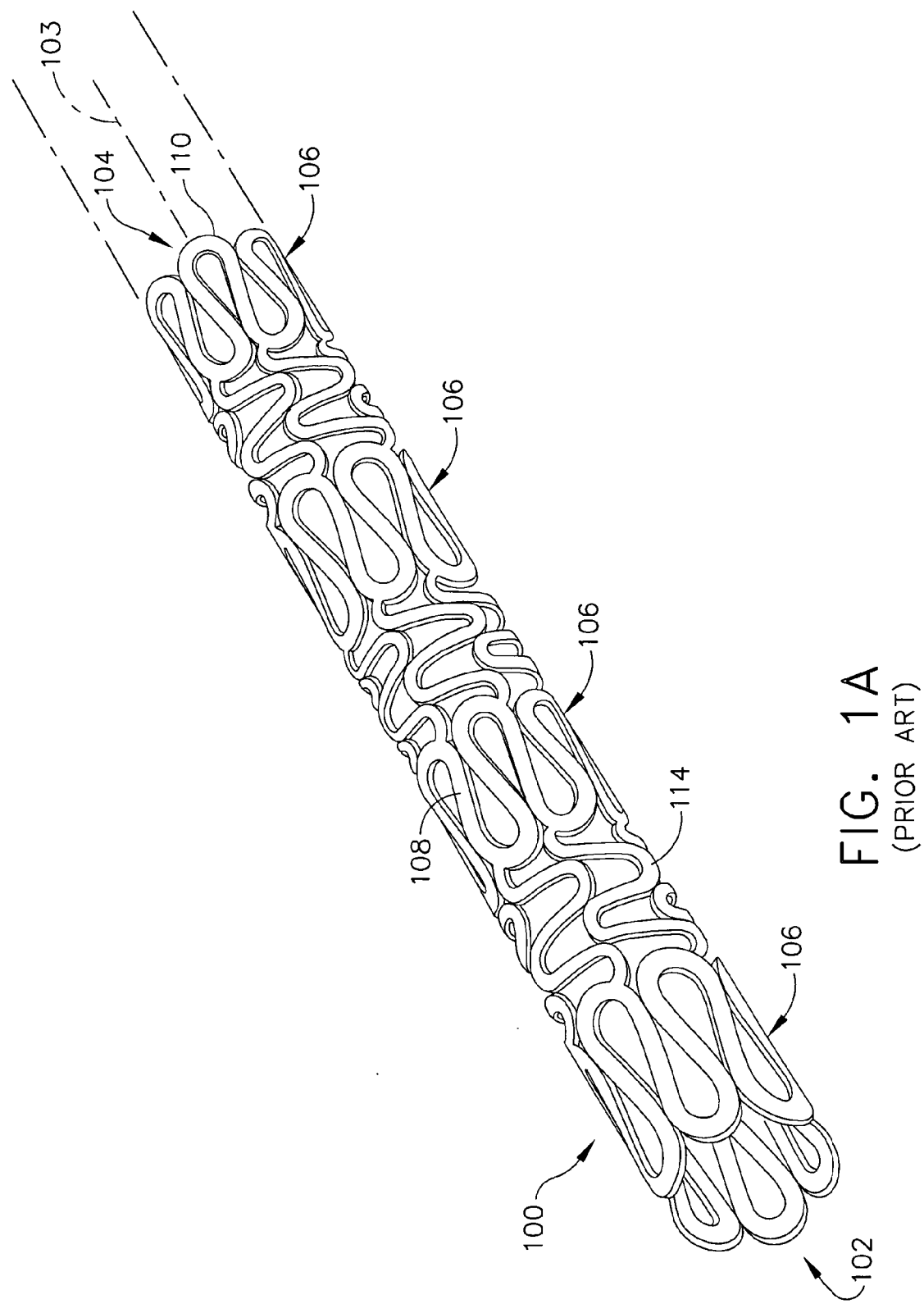
FIG. 1A is a perspective view of a prior art stent of a closed cell design in a crimped state.
Figure 2A:
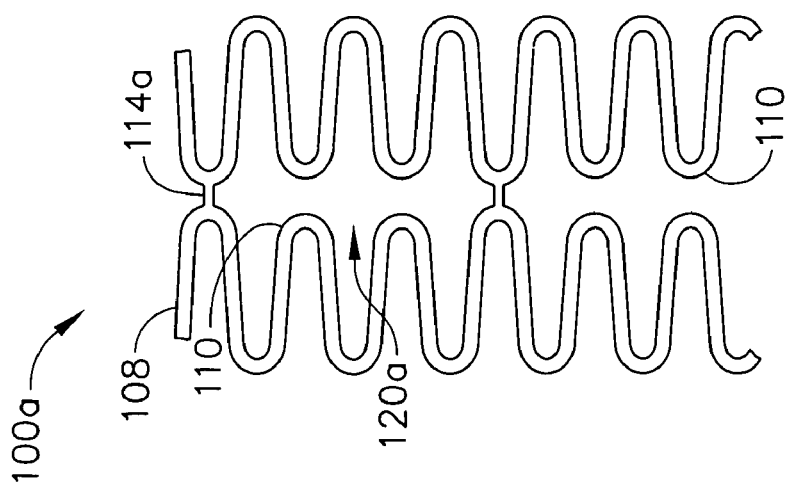
FIG. 2A is a partial side view of a prior art stent of an open-cell design in a configuration conducive for a polishing manufacturing step.
Figure 2B:
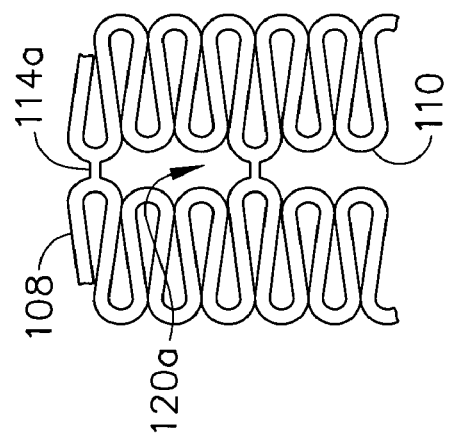
FIG. 2B is a partial side view of the prior art stent of FIG. 2A in a crimped state.
Figure 2C:
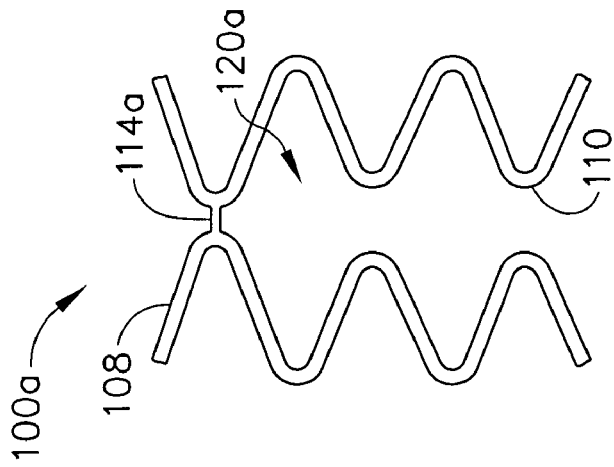
FIG. 2C is a partial side view of the prior art stent of FIG. 2A in an expanded state.

The stent 100 (FIGS. 1A-1D) and 100a (FIGS. 2A-2C) comprises an expandable lattice structure made of any suitable material which is compatible with the human body and the bodily fluids (not shown) with which the stent 100 and 100a may come into contact. The lattice structure is an arrangement of interconnecting elements made of a material which has the requisite strength and elasticity characteristics to permit the tubular shaped stent 100 and 100a to be expanded or moveable from the crimped state shown in FIGS. 1A and 1C and FIG. 2B respectively to the deployed or expanded state as shown in FIG. 1D and FIG. 2C respectively and further to permit the stent 100 and 100a to retain its expanded state at an enlarged diameter. Suitable materials for the fabrication of the stent 100 and 100a include silver, tantalum, stainless steel, cobalt-based alloys such as cobalt-chrome (L605), gold, titanium or any suitable plastic material having the requisite characteristics previously described.

The stent 100 and 100a may also comprise a superelastic alloy such as nickel titanium (NiTi, e.g., Nitinol). For stents 100 and 100a made of superelastic material, the superelastic design of the stent 100 and 100a make it crush recoverable and thus suitable as a stent or frame for any number of vascular devices for different applications.

The stent 100 and 100a comprises a tubular configuration formed by a lattice of interconnecting elements defining a substantially cylindrical configuration and having front and back open ends 102, 104 and defining a longitudinal axis 103 extending therebetween (FIG. 1A). The stent 100 (FIGS. 1A-1D) is known and has a closed-cell 120 (closed cell design) and the stent 100a (FIGS. 2A-2C) is known and has an open-cell 120a (open cell design). Characteristics of open and closed cell designs will be addressed in greater detail later in this disclosure. In its closed crimped state, the stent 100 and 100a has a first, smaller outer diameter for insertion into a patient and navigation through the vessels and, in its expanded (deployed) state, a second, larger outer diameter for deployment into the target area of a vessel with the second diameter being greater in size than the first diameter. The stent 100 and 100a comprises a plurality of adjacent hoops 106 extending between the front and back ends 102, 104. The hoops 106 include a plurality of longitudinally arranged struts 108 and a plurality of loops 110 connecting adjacent struts 108. Adjacent struts 108 are connected at opposite ends so as to form any desired pattern such as a substantially S or Z shape pattern. The plurality of loops 110 have a substantially semi-circular configuration and are substantially symmetric about their centers.

The stent 100 and 100a further comprises a plurality of flexible links or bridges 114 and 114a respectively. The bridges 114 and 114a connect adjacent hoops 106. The details of the bridges 114 and 114a are more fully described below. The term "flexible link" or "bridges" have the same meaning and can be used interchangeably. There are many types or forms for the flexible links or bridges 114. For example, the bridges 114 and 114a may be an S-Link (having an S-Shape or being sinusoidal shape), a J-Link (having a J-Shape), and N-Link (having an N-shape), M-Link (M-Shaped) or W-Link (W-Shaped), wherein each of these configurations can also be inverted.

In general, bridges 114 and 114(a) respectively are used to connect adjacent hoops 106. Each bridge comprises two ends wherein one end of the bridge is attached to a first hoop for example 106, and the other end of the bridge is attached to a second, adjacent hoop, for example 106, as shown in FIG. 1A. The attachment points for the bridge can be at any location on the hoops 106, for instance, connection points at or directly on loops 110 or struts 108. Thus, bridges that connect at every loop 110 of adjacent hoops 106, define a closed-cell as shown in FIGS. 1A-1D. Moreover, bridges that connect adjacent hoops 106 at only a select number of loops 110, e.g. a set number of loops 110 without interconnecting bridges, define an open-cell such as illustrated in FIGS. 2A-2C.

The above-described geometry distributes strain throughout the stent 100 and 100a, prevents metal to metal contact where the stent 100 and 100a is bent, and minimizes the opening between the features of the stent 100 and 100a; namely, struts 108, loops 110 and bridges 114 114a respectively. The number of and nature of the design of the struts, loops and bridges are important design factors when determining the working properties and fatigue life properties of the stent 100 and 100a. It was previously thought that in order to improve the rigidity of the stent, struts should be large, and thus there should be fewer struts 108 per hoop 106. However, it is now known that stents 100 having smaller struts 108 and more struts 108 per hoop 106 improve the construction of the stent 100 and provide greater rigidity.

FIG. 1D and FIG. 2C illustrate the stent 100 and 100a in its deployed or expanded state. As may be seen from a comparison between the stent configurations illustrated in FIG. 1C and FIG. 2B respectively and the stent configuration illustrated in FIG. 1D and FIG. 2C respectively, the geometry of the stent 100 and 100a changes quite significantly as it is deployed from its crimped state to its expanded or deployed state. As the stent undergoes diametric change, the strut angle and strain levels in the loops 110 and bridges 114 and 114a are affected. Preferably, all of the stent features will strain in a predictable manner so that the stent 100 is reliable and uniform in strength. In addition, it is preferable to minimize the maximum strain experienced by the struts 108, loops 110 and bridges 114 and 114a since Nitinol properties are more generally limited by strain rather than by stress.

With respect to stent designs in general, there are regular connections which refer to bridges 114 and 114a that include connections to every inflection point around the circumference of a structural member, i.e. the loops 110 of adjacent hoops 106.

Additionally, for stents having an open-cell design, e.g. 100a, there are periodic connections for the stent bridges 114a that include connections to a subset of the inflection points (loops 110) around the circumference of the structural members (lattice). With respect to these period connections, the connected inflection points (loops 110) alternate with unconnected inflection points (loops 110) in some defined pattern.

Moreover, in general, bridges can join the adjacent structural members at different points. For example, in a "peak-peak" connection, the bridges 114 and 114a join the adjacent structural members or loops 110 by joining the outer radii formed by adjacent loops 110. Alternatively, the bridges 114 and 114a can form "peak-valley" connections wherein the bridges 114 and 114a join the outer radii of one inflection point (of a structural member) to the inner radii of the inflection point of an adjacent structural member. Additionally "valley-valley" connections are also possible when the inner radii of inflection points of adjacent structural members are joined.

Furthermore, the bridges 114 and 114a between adjacent structural members, i.e. hoops 106, define cell patterns as briefly mentioned above. For example, bridges 114 may define a "closed-cell" formed where all of the internal inflection points, e.g. loops 110 are connected by bridges 114 as shown in FIGS. 1A-1D.

Furthermore, it is common for bridges 114 to form a "closed-cell" which is in essence a sequential ring construction wherein all internal inflection points of the structural members are connected by bridges 114. The closed-cells permit for plastic deformation of the stent 100 during bending thereby allowing adjacent structural members to separate or nest together in order to more easily accommodate changes in shape of the stent 100. The primary advantages of a closed-cell stent design is that it provides optimal scaffolding and a uniform surface regardless of the degree of bending of the stent. Depending on the specific features of a closed-cell design, the stent 100 may be less flexible than a stent with an open-cell design.

Figure 3A:
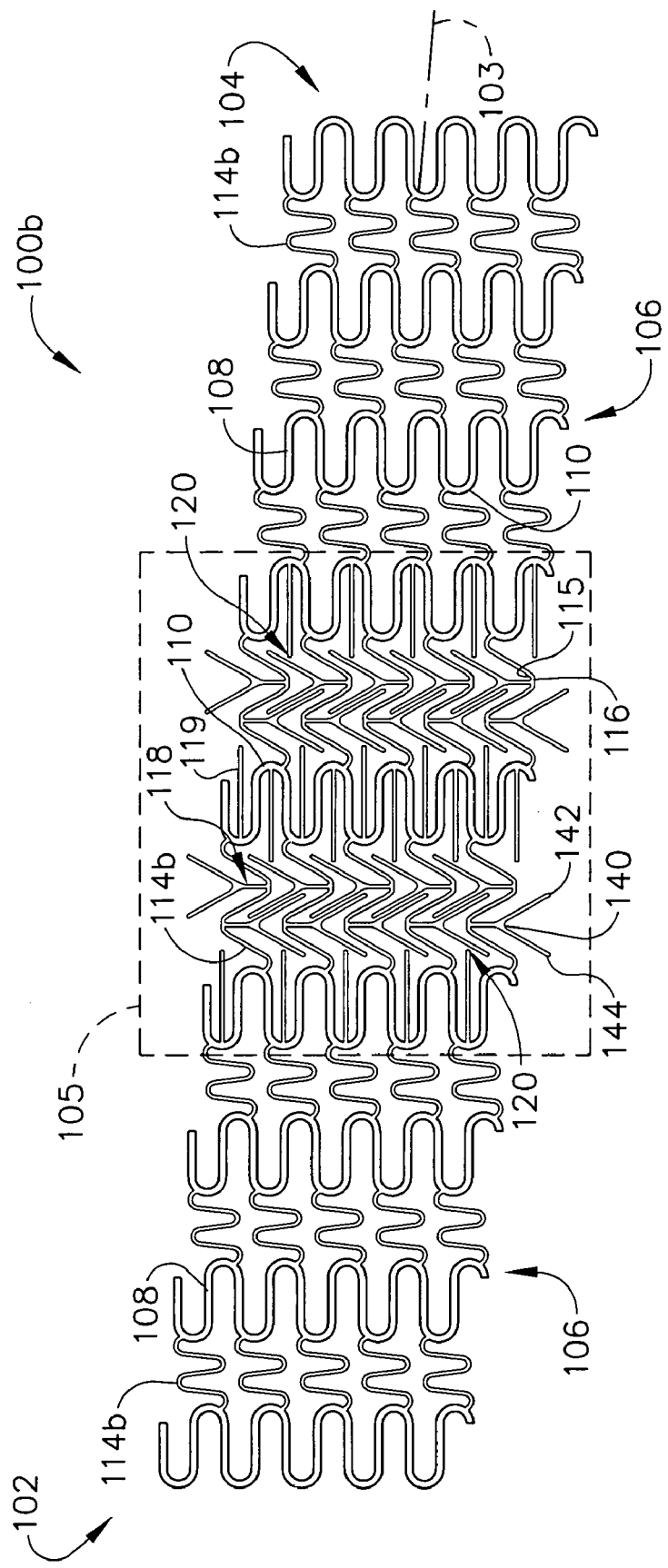
FIG. 3A is a side view of a stent as a closed-cell design having an open area center section and one or more extensions in accordance with the present invention.
Figure 3B:
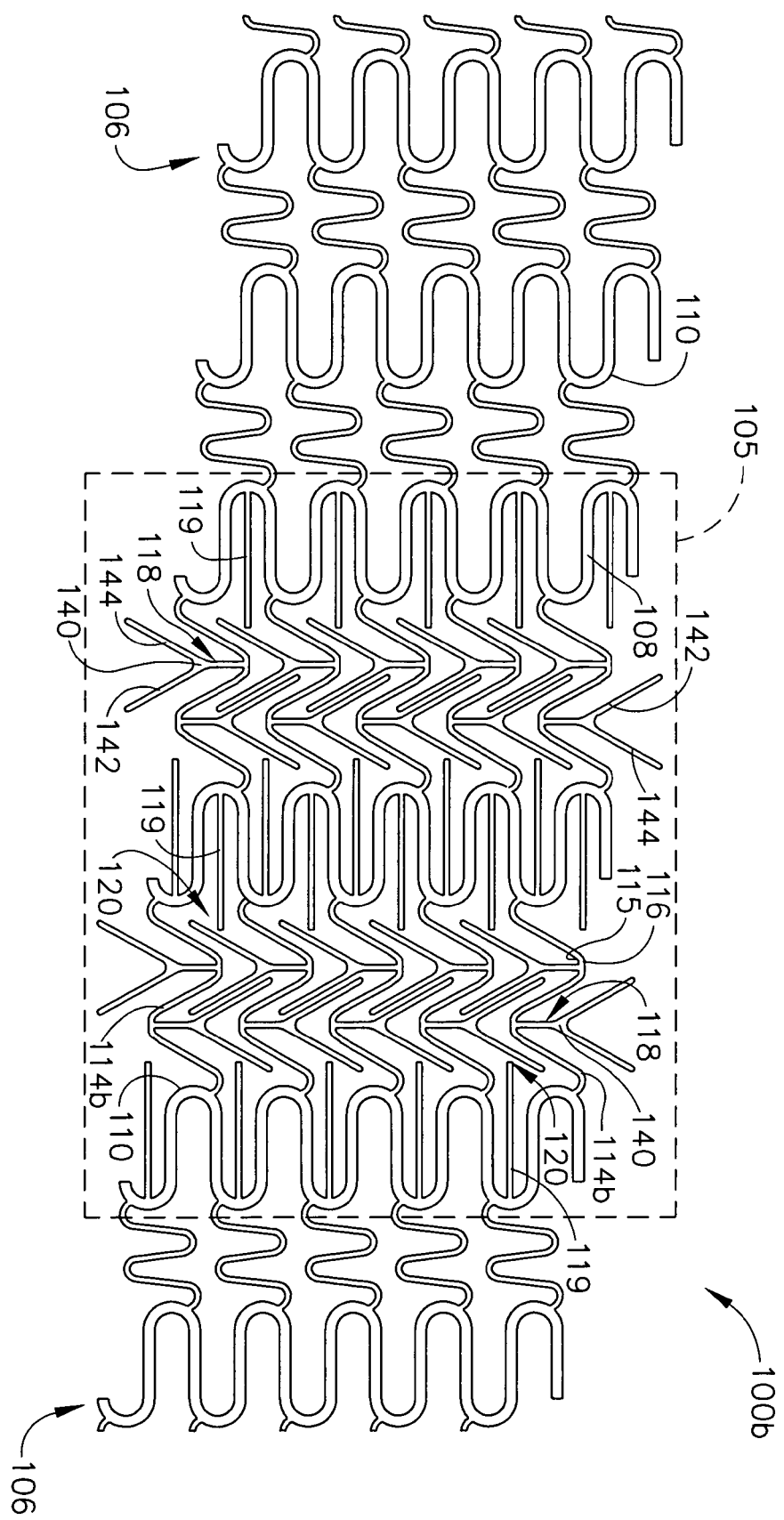
FIG. 3B is an enlarged partial side view of the stent of FIG. 3A in accordance with the present invention.

Turning now to the present invention, the same reference numerals will be used to designate like or similar features for a stent 100b (FIGS. 3A-3E), and 100c (FIGS. 4A-4E) in accordance with the present invention as best illustrated in these figures. One novel stent 100b in accordance with the present invention is a closed-cell design stent as best illustrated in FIGS. 3A and 3B. By way of example, the stent 100b has a center section, center portion, center segment, middle section, middle portion or middle segment (all used interchangeably herewith) 105 that contains and utilizes bridges 114b that connect every loop 110 of adjacent hoops 106. By way of example, the bridge 114b is shown as a sinusoidal-shaped bridge, however, the bridge 114b can comprise any particular shape or configuration such as the shapes addressed above.

Each bridge 114b has a finger or extension 118 integrally formed therewith and contiguous with the bridge 114b. In accordance with the present invention, the extension 118 is a finger or finger-like projection from the bridge 114b. Each bridge 114b can include more than one extension 118 extending therefrom. For instance, the sinusoidal-shape bridge 114b includes one or more apex 116 and a pocket 115, which is a space directly beneath or underlying the apex 116 as shown. In this example, the extensions 118 are linear projections and extend from pocket 115 of an adjacent bridge 114b. Extensions 118 and side extensions 119 (described in detail below) are located at any desired location for the stent 100b such as proximal end sections, segments or portions 102, distal end sections, segments or portions 104 and center sections, segments or portions 105. Preferably, extensions 118 and side extensions 119 are located in center section 105 of stent 100b.

The extensions 118 extend from each pocket 115 of bridge 114b and are designed as cantilevered projections that are expandable or movably deformable in a direction away from bridge 114b by balloon force or by shape memory or the like during a side branch access procedure, for instance, treating lesions and supporting tissue in a vessel bifurcation, vessel trifurcation or a vessel having more than two side branches as well as treating lesions and supporting tissue in a bifurcation of a vessel bifurcation such as treatment and/or supporting of the iliac arteries or the like. The extension 118 has a center arm terminating in a bifurcation 140. Each bifurcation 140 further includes at least one arm, for instance, a first arm 142 and a second arm 144. The arms 142 and 144 can have different dimensions, for instance, the first arm 142 is shorter in length than the second arm 144 or vice versa, i.e. first arm 142 is greater or longer in length than second arm 144. Alternatively, the extensions 118 project from the apex 116 of the bridge 114b (not shown).

Additionally, side extensions 119 are located on each pocket of adjacent loops 110 and project into the cells 120 located in center or middle section 105 of the stent 100b. For efficiency purposes, such as ensuring compactness and low profile for crimping the stent 100b onto its delivery device or catheter, the bifurcation 140 is shaped to receive and accommodate the apex 116 of an adjacent bridge 114b. Thus, adjacent bridges 114b will have adjacent extensions 118 that nest with each other when the stent 100b is in the crimped state. The side-by-side alignment of adjacent extensions 118 of adjacent bridges 114b is facilitated by the shape of the bridges (in this example a sinusoidal shape embodiment) whereby at the underside of each apex 116 resides a bridge pocket 115 of sufficient size and configuration in order to receive and accommodate the extension (finger) 118. At a minimum, the apex 116 of one bridge 114b will fit within the arms 142 and 144 of bifurcated 140 of extension 118 of an adjacent bridge 114b in the crimped state.

Additionally, the stent 100b has a center or middle portion or center or middle section 105 (designated by dashed lines) that has greater spacing (more open spaced area) between adjacent hoops 106 than the spacing (or size of open space areas) at or near the proximal end section or segment 102 and the distal end section or segment 104 respectively of the stent 100b. Thus, the cells 120 of center section or portion 105 have a greater spacing between adjacent hoops 106, than the spacing of the cells between adjacent hoops 106 at or near the proximal end section 102 and the distal end section 104 respectively.

Figure 3C:
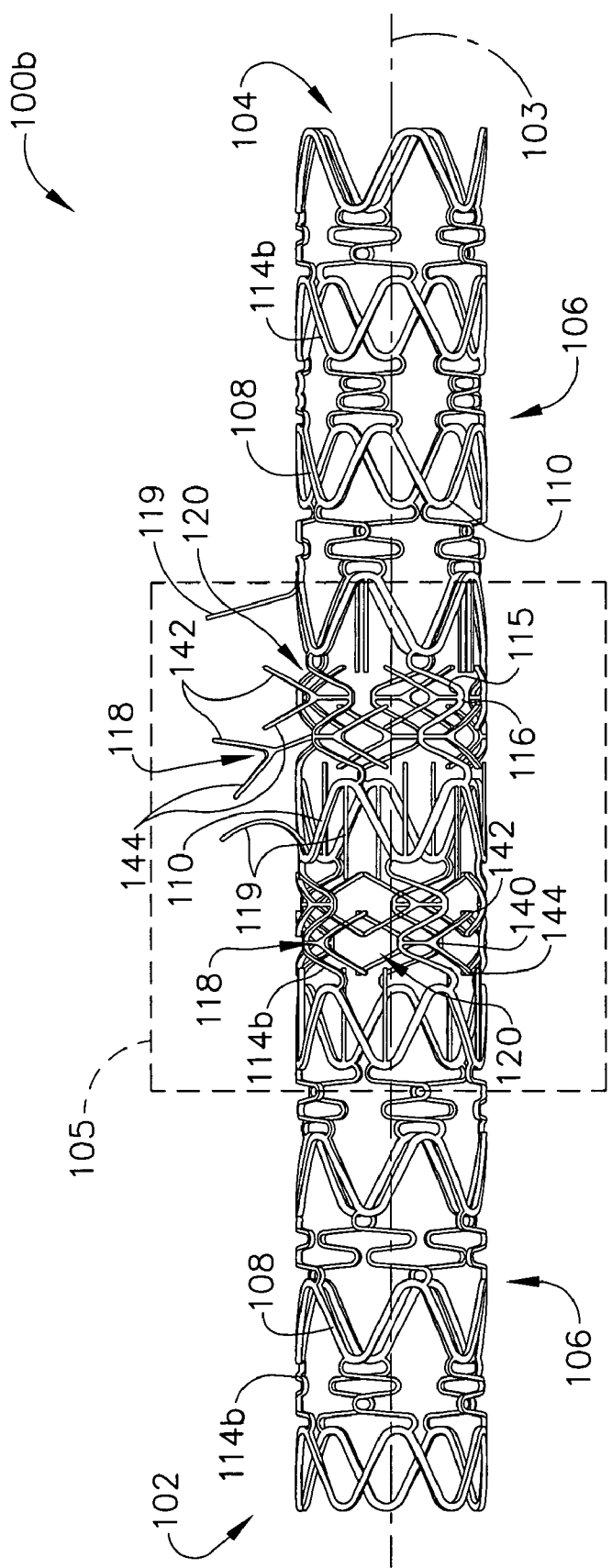
FIG. 3C is a perspective view of the stent of FIG. 3A in isolation after undergoing a cell dilation procedure in accordance with the present invention.
Figure 3D:
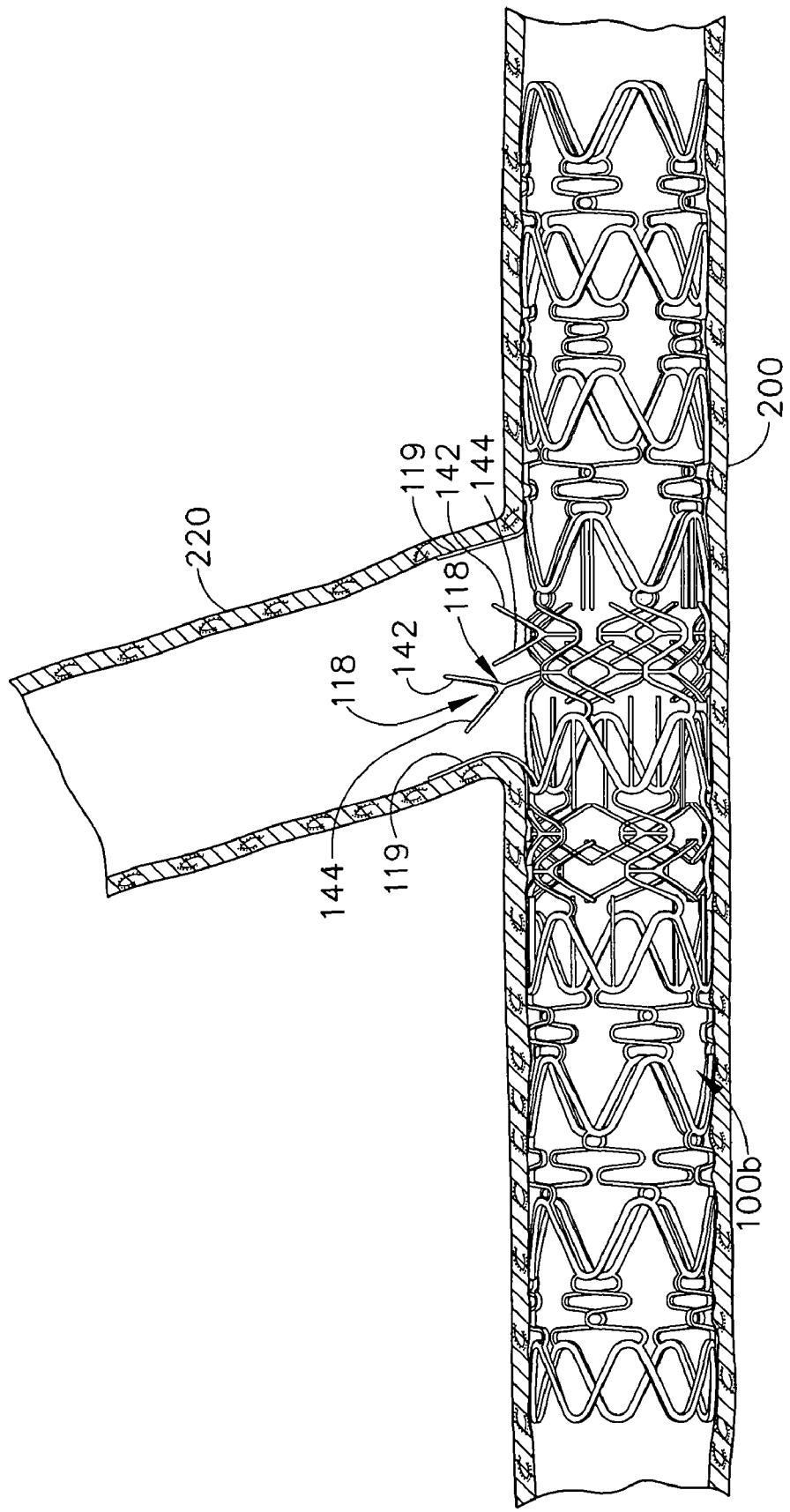
FIG. 3D is a perspective view of the stent of FIG. 3A in a main vessel after undergoing a cell dilation procedure in accordance with the present invention.

A major advantage of the open-spaced center section 105 in one embodiment in accordance with the present invention, is that after the stent 100b is expanded in a vessel, such as a main or trunk vessel 200, it may be desirable to conduct a cell dilation procedure, for example, a side branch access procedure such as shown in FIGS. 3A-3E. Accordingly, the cell 120 itself is required to be dilated. Thus, when the cell 120 of the stent 100b is dilated through a cell dilation procedure, for example, a side branch access procedure, the cell 120 is dilated, in one embodiment, by placing a balloon within cell 120 in the center section 105 and inflating the balloon within the cell 120. As the cell 120 is dilated, the extensions 118 and 119 are moved in a direction away from the bridge 114b and loop 110 respectively as shown in FIG. 3C. Extensions 118 and 119 are designed to deform such that the extensions 118 and 119 come into supporting contact with the tissue of a vessel side branch 220 upon dilation of the cell 120 as shown in FIG. 3D. This deformation causes an enlarged surface area for supporting the vessel side branch because the extension 118, due to its bifurcated 140 and side arms 142 and 144, facilitates good contact and supporting surface for the vessel side branch. The extension 119 also provides additional contact and supporting surface area for the vessel side branch upon dilation of the cell 120. These same advantages are afforded to the open-cell design stent 100c (FIGS. 4A-4E) in accordance with the present invention. Moreover, in another embodiment according to the present invention, the stent 100b and 100c (FIGS. 3A-3E) and (FIGS. 4A-4E) respectively are self-expanding stents made of a shape memory material such as NiTi and the cell 120 (FIGS. 3C-3E) and the cell 120a (FIGS. 4C-4E, addressed in greater detail below) are dilated by the shape memory aspect of the lattice features defining the cell, i.e. no separate balloon dilation step is required, but rather, the cell 120 and 120a respectively is dilated based on shape memory properties alone, to include deformation of the extensions 118 and 119 away from the lattice at the cell 120 and 120a respectively.

Additionally, the extensions 118 and 119 can be located on any of the loops 110, and struts 108 as well as the bridges 114b or in any combination thereof.

In accordance with the present invention, the stent 100b (FIGS. 3A-3E), and stent 100c (FIGS. 4A-4E), have extensions 118 and 119 respectively located on one or more of the following components of the center section 105 of the stent lattice in one embodiment of the invention: the bridges 114b, the hoops 106, the loops 110, and/or the struts 108. Additionally, in another embodiment of the invention, extensions 118 and 119 are located on one or more of these stent features of the proximal end section 102, the center section 105 and the distal end section 104 in any combination, i.e. extensions 118 and 119 located on the entire length of the stent or located on one or more of the sections 102, 104 and 105. Moreover, the components of the stent lattice and the extensions 118 and 119 respectively have drug coatings or drug and polymer coating combinations that are used to deliver the drug, i.e. therapeutic and/or pharmaceutical agents including:

antiproliferative/antimitotic agents including natural products such as vinca alkaloids (i.e. vinblastine, vincristine, and vinorelbine), paclitaxel, epipodophyllotoxins (i.e. etoposide, teniposide), antibiotics (dactinomycin (actinomycin D) daunorubicin, doxorubicin and idarubicin), anthracyclines, mitoxantrone, bleomycins, plicamycin (mithramycin) and mitomycin, enzymes (L-asparaginase which systemically metabolizes L-asparagine and deprives cells which do not have the capacity to synthesize their own asparagine); antiplatelet agents such as $G(GP)II_bIII_a$ inhibitors and vitronectin receptor antagonists;

antiproliferative/antimitotic alkylating agents such as nitrogen mustards (mechlorethamine, cyclophosphamide and analogs, melphalan, chlorambucil), ethylenimines and methylmelamines (hexamethylmelamine and thiotepa), alkyl sulfonates-busulfan, nirtosoureas (carmustine (BCNU) and analogs, streptozocin), trazenes-dacarbazinine (DTIC); antiproliferative/antimitotic antimetabolites such as folic acid analogs (methotrexate), pyrimidine analogs (fluorouracil, floxuridine, and cytarabine), purine analogs and related inhibitors (mercaptopurine, thioguanine, pentostatin and 2-chlorodeoxyadenosine {cladribine}); platinum coordination complexes (cisplatin, carboplatin), procarbazine, hydroxyurea, mitotane, aminoglutethimide; hormones (i.e. estrogen); anticoagulants (heparin, synthetic heparin salts and other inhibitors of thrombin); fibrinolytic agents (such as tissue plasminogen activator, streptokinase and urokinase), aspirin, dipyridamole, ticlopidine, clopidogrel, abciximab; antimigratory; antisecretory (breveldin); antiinflammatory: such as adrenocortical steroids (cortisol, cortisone, fludrocortisone, prednisone, prednisolone, 6α-methylprednisolone, triamcinolone, betamethasone, and dexamethasone), non-steroidal agents (salicylic acid derivatives i.e. aspirin; para-aminophenol derivatives i.e. acetominophen; indole and indene acetic acids (indomethacin, sulindac, and etodalac), heteroaryl acetic acids (tolmetin, diclofenac, and ketorolac), arylpropionic acids (ibuprofen and derivatives), anthranilic acids (mefenamic acid, and meclofenamic acid), enolic acids (piroxicam, tenoxicam, phenylbutazone, and oxyphenthatrazone), nabumetone, gold compounds (auranofin, aurothioglucose, gold sodium thiomalate); immunosuppressives:

(cyclosporine, tacrolimus (FK-506), sirolimus (rapamycin), azathioprine, mycophenolate mofetil); angiogenic agents: vascular endothelial growth factor (VEGF), fibroblast growth factor (FGF) platelet derived growth factor (PDGF), erythropoetin, angiotensin receptor blocker; nitric oxide donors; anti-sense oligionucleotides and combinations thereof; cell cycle inhibitors, mTOR inhibitors, and growth factor signal transduction kinase inhibitors. It is important to note that one or more of the lattice components (e.g. hoops, loops, struts, bridges and extensions) are coated with one or more of the drug coatings or drug and polymer coating combinations.

Additionally, stent 100b and 100c in accordance with the present invention are made of any material such as metal alloys, nickel titanium alloys such as NiTi, including deformable metal alloys or plastics, metal alloys or plastics that exhibit crushing or recoil upon deployment of the stent or polymer materials such as biodegradable polymers and/or bioabsorbable polymers. Thus, the entire stent 100b and 100c itself (all components) or selectable components of the stent 100b and 100c in accordance with the present invention can be made of any of these type of materials to include plastics or polymers to include biodegradable polymers and/or bioabsorbable polymers. Additionally, the biodegradable polymers and/or bioabsorbable polymers used as material for stent 100b and 100c can be drug eluting polymers capable of eluting a therapeutic and/or pharmaceutical agents according to any desired release profile.

As illustrated in FIGS. 3A-3E and 4A-4E, the extensions 118 and 119 are cantilevered projections and terminate in a free end (not connected to the stent lattice, e.g. connected at only one end to the stent lattice) that are movably deformable away from the stent lattice and longitudinal axis of stent 100b and 100c when the stent is deployed to its expanded or deployed state. In accordance with the present invention, the extension 118 and 119 can comprise a different material from the remainder of the components used for the stent lattice (for instance the hoops, loops, struts and bridges) especially if a different stiffness is desired.

Figure 4A:
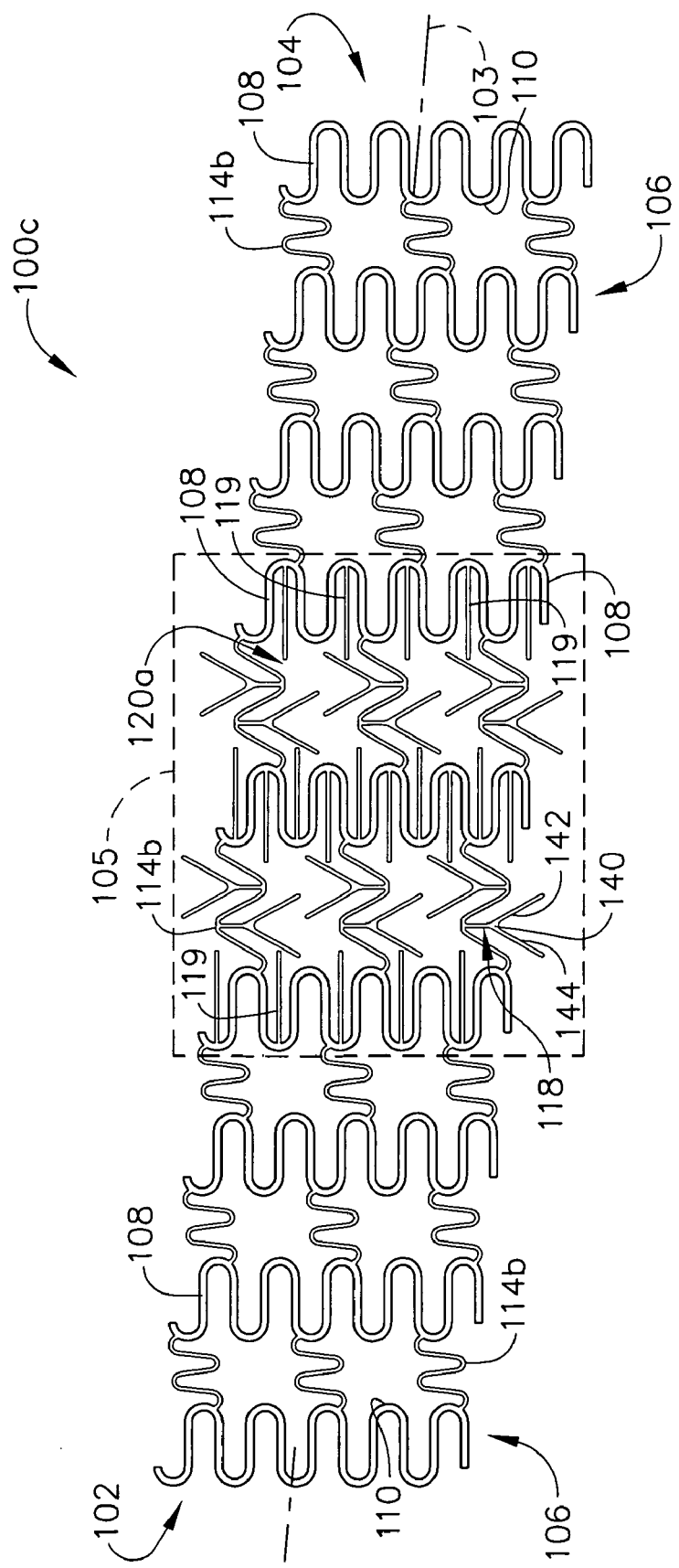
FIG. 4A is a partial side view of a stent as an open-cell design having an open area center section and one or more extensions in accordance with the present invention.
Figure 4B:
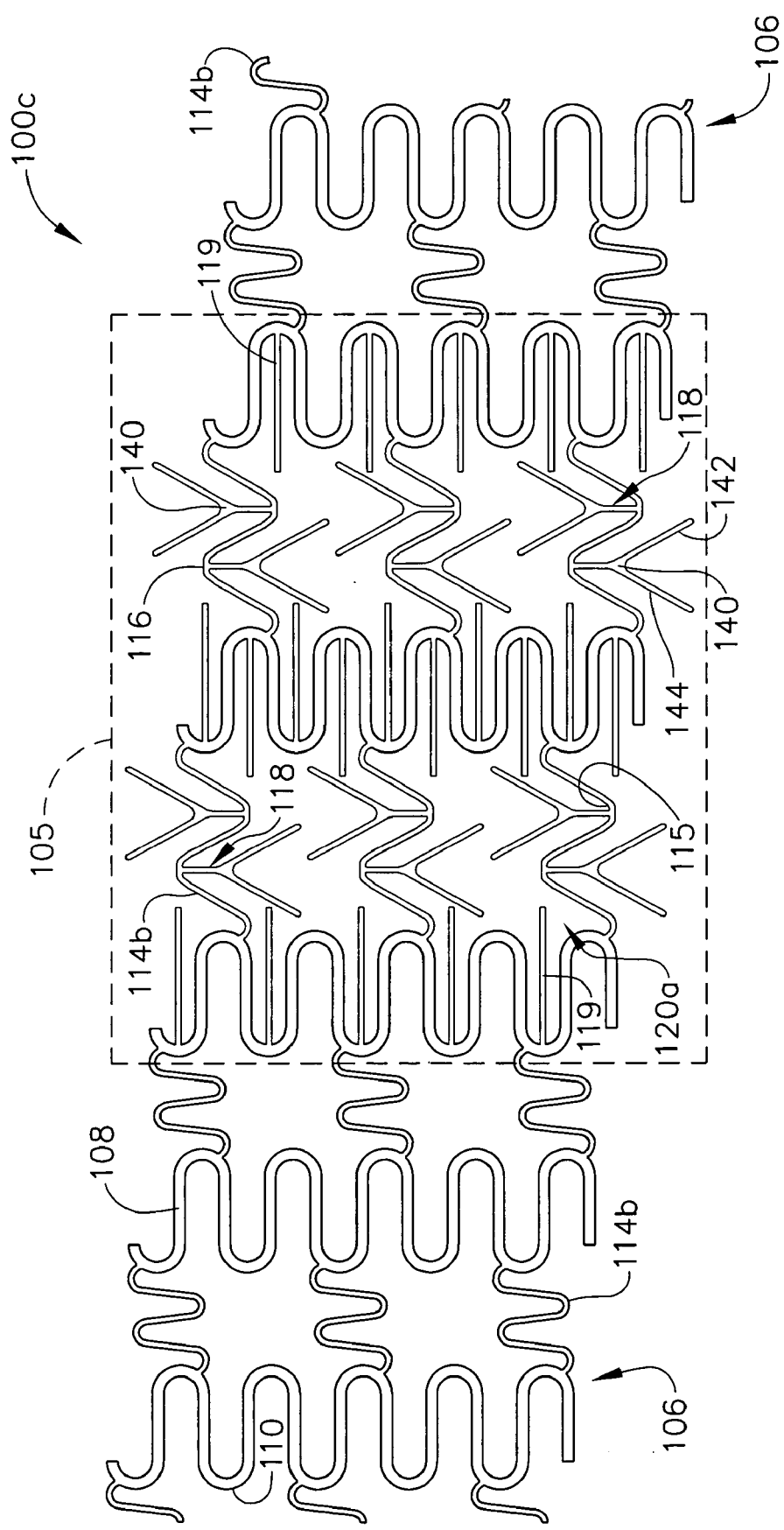
FIG. 4B is an enlarged partial side view of the stent of FIG. 4A in accordance with the present invention.
Figure 4C:
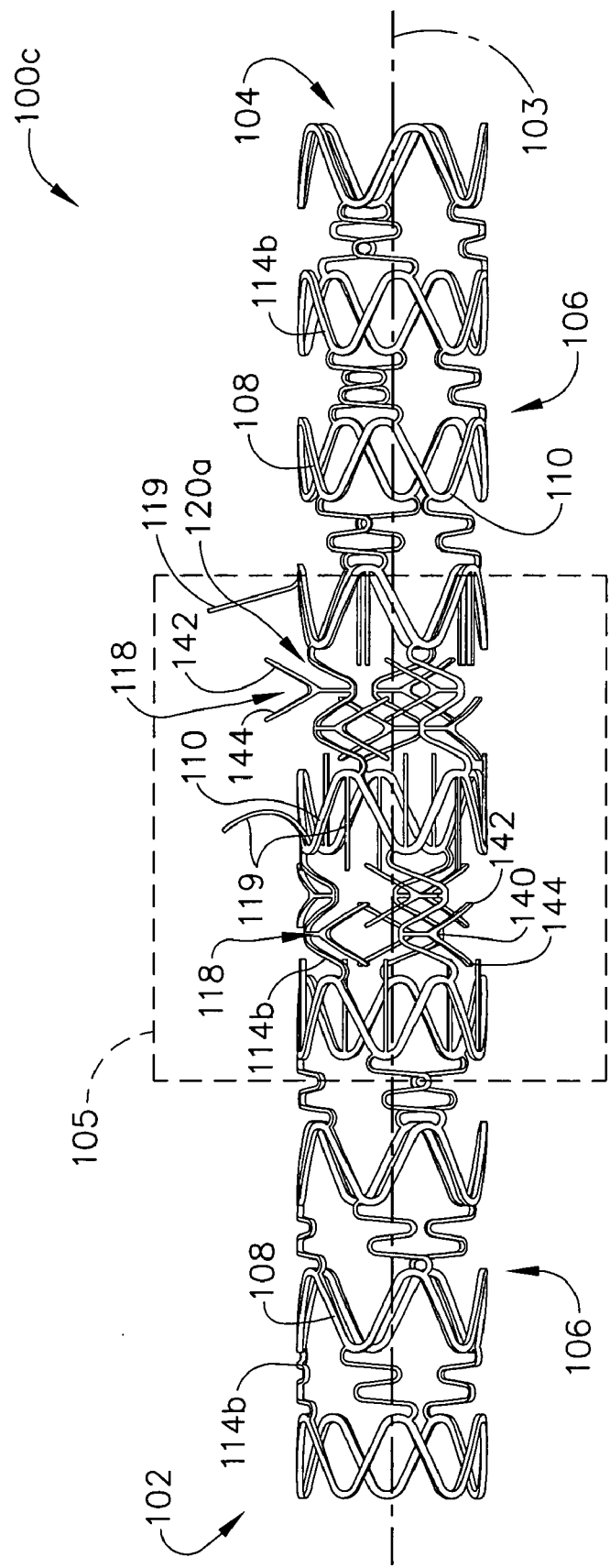
FIG. 4C is a perspective view of the stent of FIG. 4A in isolation after undergoing a cell dilation procedure in accordance with the present invention.

As shown in FIGS. 4A and 4B, the stent 100c in accordance with the present invention is an open-cell design stent also having a center section 105. The center section 105 has a plurality of cells 120a having extensions 118 (connected to bridges 114b) and side extensions 119 connected at the inner most portion of the loops 110 (for example at the apex of loop 110). Accordingly, the cells 120a of the center section 105 of stent 100c have a larger open-spaced area (defined as the spacing between adjacent hoops 106) when compared to the open spaced areas associated with cells at or near proximal end section 102 and distal end section 104 respectively.

The same features and functionality as described above for the stent 100b also apply to the stent 100c in accordance with the present invention with the exception that the stent 100c is of an open-cell design.

As mentioned above, the extensions 118 and 119 enhance the overall surface area of the stent 100b and 100c respectively especially when the cell 120 is dilated as part of a cell dilation procedure for establishing vessel side branch access. The increased surface area within the space or area defined by the stent lattice including the extensions 118 and 119, provides not only a significant advantage in preventing the prolapse of plaque or tissue into the cell 120a and ultimately into the lumen of the stent (100b and 100c) when deployed within a vessel 200, i.e. at the site of a lesion within the vessel, but also provides support for the tissue of the vessel branch 220 thereby preventing "jailing" and maintaining good open patency of the vessel side branch 220. Accordingly, the extensions or fingers 118 and 119 respectively in accordance with the present invention inhibit this prolapse phenomena thereby providing a prevention barrier against restenosis of the vessel 200 at the lesion site as well as permit good blood flow through the vessel side branch 220. Additionally the extensions or fingers 118 and 119 are good for localized drug delivery to a very common site for restenosis in bifurcations, namely the vessel carina and/or ostium.

In accordance with the present invention, the extensions or fingers 118 and 119 respectively may also take the form of other shapes and patterns.

Additionally, the stent 100b and 100c in accordance with the present invention may be made from various materials such as those referred to above. For example, the stent 100b and 100c is made of an alloy such as stainless steel. Moreover, the stent 100b and 100c is alternatively made of a crush-recoverable material such as a superelastic material or superelastic alloy or combination of alloys. In particular, the stent 100b and 100c is made of nickel titanium (NiTi) or nickel titanium tertiary alloys thereby providing it with superelastic and crush recoverable properties as a self-expanding stent. Preferable materials include those which are plastically deformable like stainless steel and cobalt-chrome.

Figure 4D:
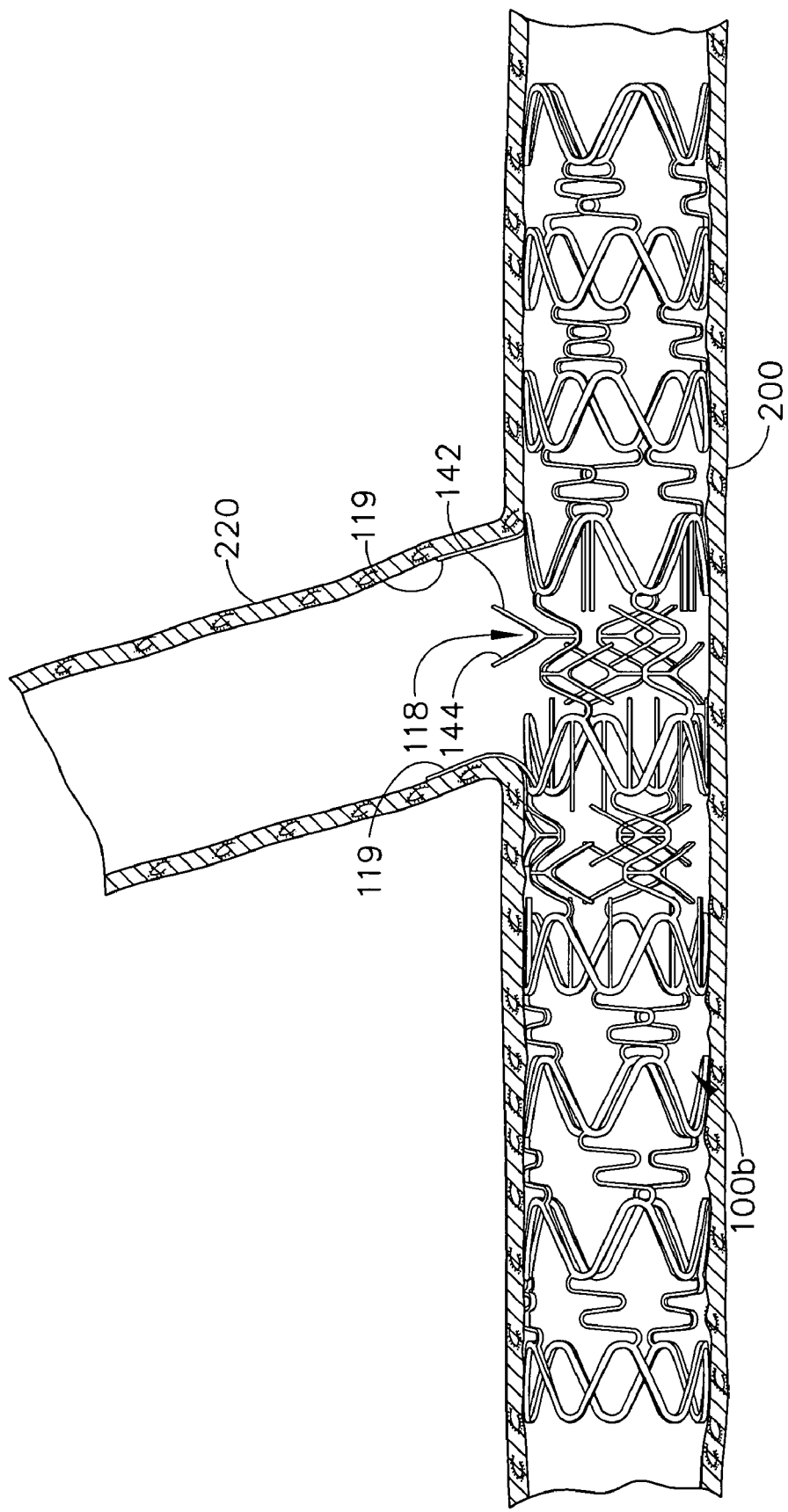
FIG. 4D is a perspective view of the stent of FIG. 4A in a main vessel after undergoing a cell dilation procedure in accordance with the present invention.

As mentioned previously, a major advantage of the extensions 118 and 119 respectively, is that the extensions provide enhanced and/or additional coverage and support at the ostium and carina of a vessel side branch 220 (FIGS. 3D and 4D respectively) with either a closed-cell or the open-cell stent 100b and 100c respectively when the stent 100b and 100c undergo a dilation of the cell 120a as part of a vessel side-branch access procedure such as the one briefly described above. Thus, upon dilation of a cell 120a, for example in the center section 105 of stent 100b and 100c respectively, the extensions 118 and 119 respectively are cleared from flow passage at the vessel side branch 220 due to balloon expansion (in one embodiment of the invention or by shape memory deformation in another embodiment of the invention), and the cantilevered extensions 118 and 119 respectively are moved away from the lattice and cell 120a into a support position (by the balloon expansion or by shape memory deformation respectively) against the tissue of the vessel side branch 220 for directly supporting the side branch vessel 220 thereby forming a stable graft at the main vessel 220 and side branch vessel 220 junction as illustrated in FIGS. 3D and 4D respectively.

Method For Accommodating Vessel Side Branches

As best illustrated in FIGS. 3D and 3E and FIGS. 4D and 4E respectively, the novel method for accommodating vessel side branches and avoiding stent jailing problems in accordance with the present invention comprises identifying a vessel 200 to be treated with a stent, for instance by using stent 100b and 100c and placing the stent 100b and 100c at a site within the target vessel 200. By way of example, the target vessel can be either a main vessel or trunk vessel 200 of any artery or one of the minor side branches 220 extended therefrom.

Additionally, a determination is made as to whether or not any connecting vessels adjacent the site in the targeted vessel also require stent placement. This determination can be made either with prior to placement of the stent 100b and 100c in the target vessel or after placement of the stent 100b and 100c at the site. Placement of a second stent 100b and 100c in one of the side branch vessels 220 or vessels 220 connecting the target vessel 200 after placement of a first stent 100b and 100c in the main or trunk vessel 200 or the initial or first vessel 200 is made for purposes such as treating disease such as stenosis, vulnerable plaque, ischemic heart disease or the like or for establishing or re-establishing patency of a side branch vessel 220 or second vessel 220 by removing obstructions at the ostia of the side branch vessel or second vessel which may be caused one of the elements or features of the lattice of stent 100b and 100c, i.e. a "jailing" problem or by displaced tissue of any one of the vessels such as intima at the ostia of the side branch vessel 220 or second vessel 220.

Preferably, when placing stent 100b and 100c in the main vessel 200 or trunk vessel 200 (the initial vessel or first vessel to be stented) the center section 105 of the stent 100b and 100c is aligned at, near or over the ostium of the side branch vessel 220 or second vessel 220 interconnecting the main vessel or first vessel 200.

Accordingly, after placement of the first stent 100b and 100c, within the main vessel or first vessel 200 and alignment of a cell 120 and 120a within center section 105 at, near or over the ostium of the side branch vessel or second vessel 220, the cell 120 and 120a is identified and expanded, for example, by inserting a catheter having an expansion device such as a balloon and inflating the balloon such that the cell 120 and 120a is expanded or dilated to a larger size (when compared to the size of cell 120 and 120*a* after initial placement and prior to dilation of the cell 120 and 120*a*, i.e. an initial smaller size), or in an alternative embodiment according to the present invention, the lattice portions defining the cell 120 and 120*a*, i.e. the adjacent hoops 106 and bridges 114*b*, are expanded as part of the self-expanding material of the stent 100*b* and 100*c* to include self-expansion of the extensions 118 and 119 upon deployment of stent 100*b* and 100*c* to its expanded state or expanded configuration.

Dilation of cell 120*a* at the ostium of the side branch vessel or second vessel 220 is accomplished by exerting force upon the one or more of the components of the lattice defining cell 120*a* for the stent 100*b* and 100*c* such as the hoops 106, the loops 110, the struts 108, the bridges 114*b*, the extensions 118 and 119, the bifurcations 140, and the arms 142 and 144. Accordingly, an expansion device, such as a catheter having an inflatable balloon is inserted into the cell 120*a* such as being inserted at a location adjacent or near one or more of lattice components such as those described above. Inflation of the balloon exerts the requisite force on the one or more cell defining components of the lattice.

Moreover, upon dilation of cell 120*a*, for example, through balloon dilation, the components of the lattice are moved away from the cell 120*a* as shown in FIGS. 3C and 3D and FIGS. 4C and 4D respectively. Particularly, the cantilevered extensions 118 and 119 are moved away from the bridge 114*b* and loop 110 respectively (moved away from longitudinal axis of stent 100*b* and 100*c*). The extensions 118 and 119 are designed such that portions of the surface area of the extension 118 (such as the center arm, the bifurcation 140 and arms 142 and 144) and extension 119 contact and support the vessel wall of the side branch vessel or second vessel 220, particularly at the ostium thereby providing additional support for the side branch vessel or second vessel 220 and thereby preventing prolapse of this tissue at the vessel bifurcation and thereby preventing jailing of the side branch vessel or second vessel 220.

Figure 3E:
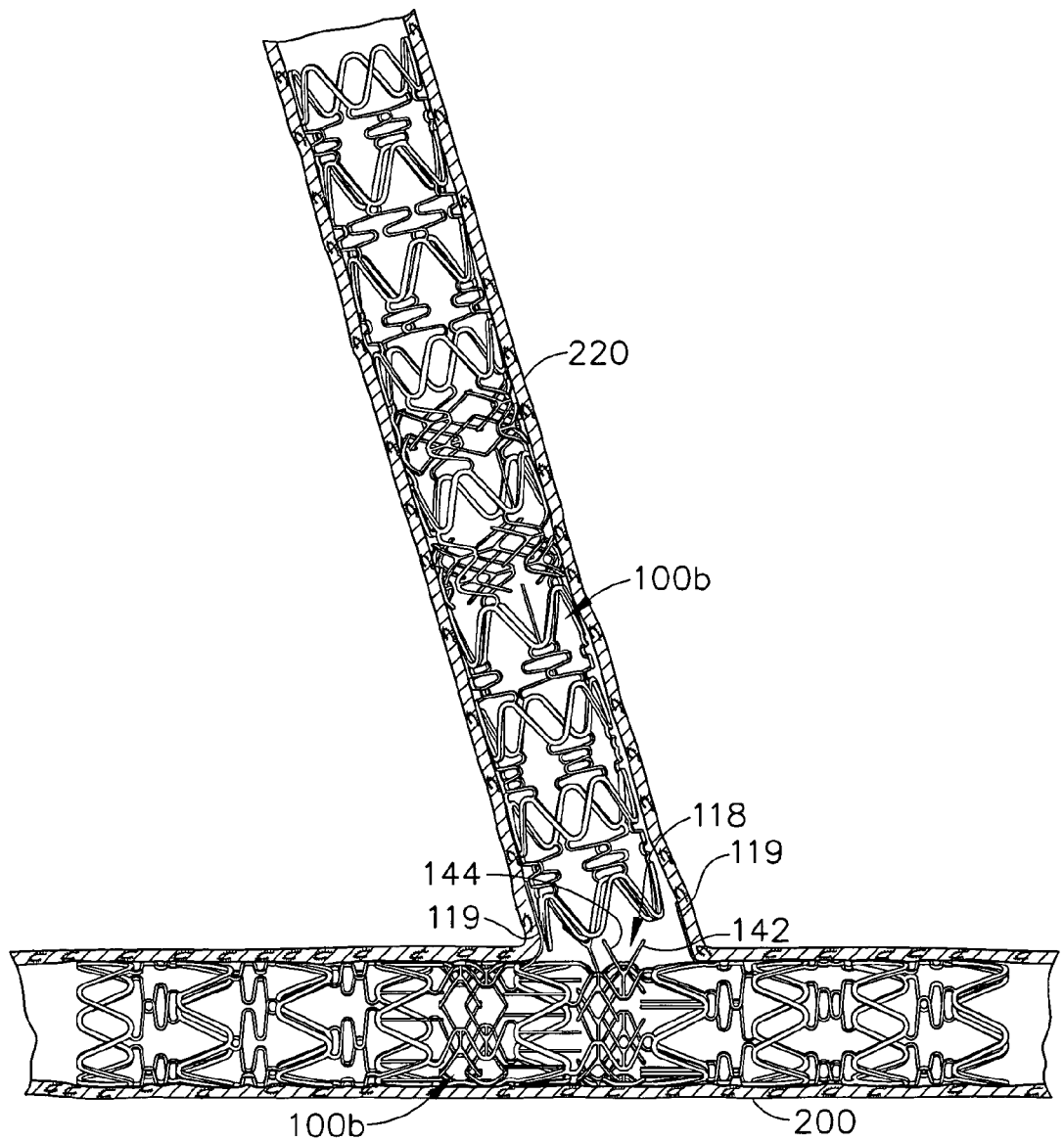
FIG. 3E is a perspective view of the stents of FIG. 3A in both a main vessel and a branch vessel in accordance with the present invention.
Figure 4E:
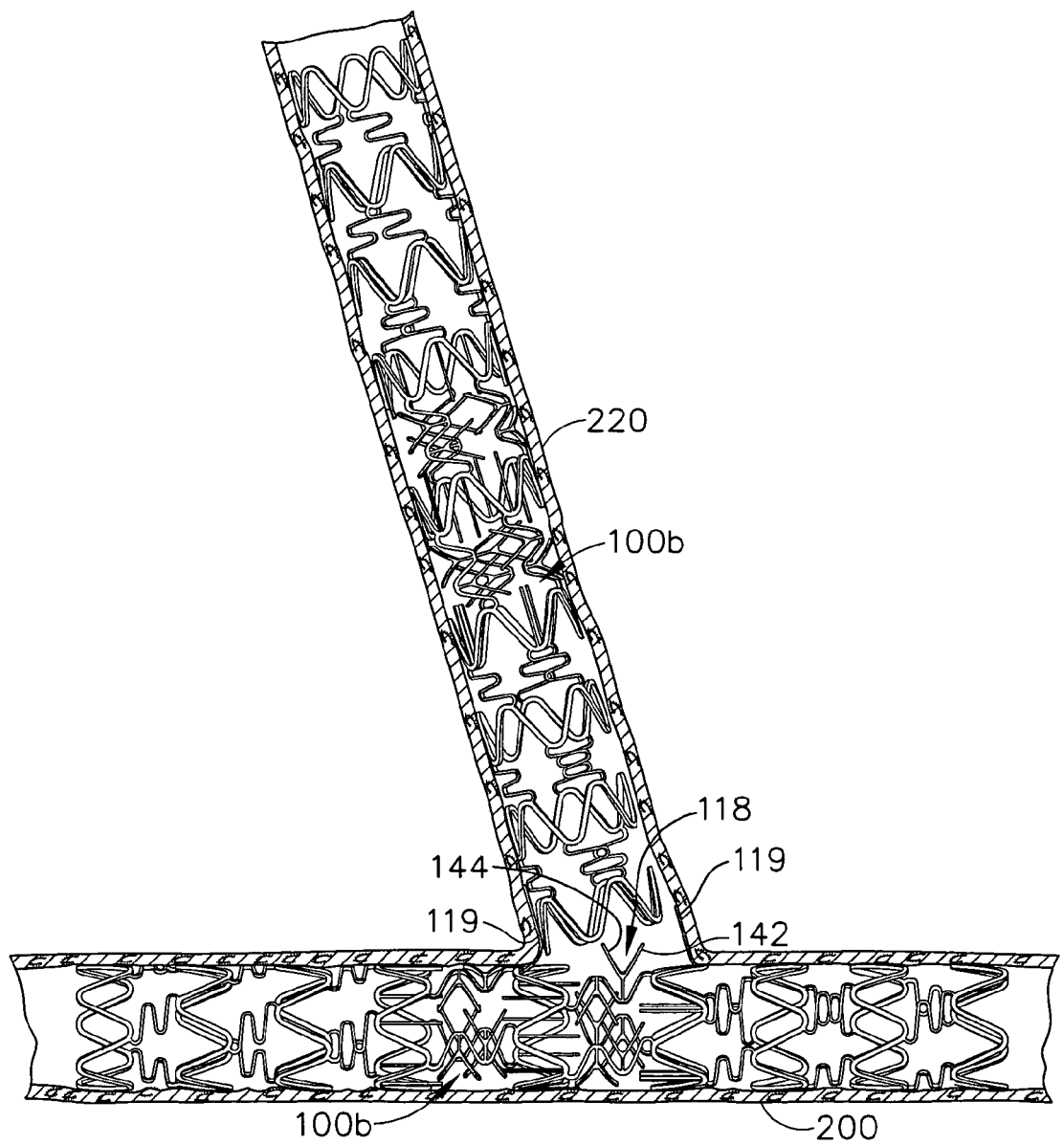
FIG. 4E is a perspective view of the stents of FIG. 4A in both a main vessel and a branch vessel in accordance with the present invention.

As best illustrated in FIGS. 3E and 4E respectively, after dilating cell 120*a*, a second stent 100*b* and 100*c* in accordance with the present invention, is placed, in the side branch vessel or second vessel 220, i.e. at the ostium of the side branch vessel or second vessel 220. The second stent 100*b* and 100*c* is placed either simultaneously with dilation of the cell 120*a* by deployment of the second stent 100*b* and 100*c* upon inflation of the balloon or after dilation of the cell 120*a* through use of a second delivery device, such a catheter, carrying the second stent 100*b* and 100*c*.

While preferred embodiments of the present invention have been shown and described herein, it will be obvious to those skilled in the art that such embodiments are provided by way of example only. Numerous variations, changes, and substitutions will now occur to those skilled in the art without departing from the invention. Accordingly, it is intended that the invention be limited only by the spirit and scope of the appended claims.

What is claimed is:

1. A stent comprising:
   a lattice defining a substantially cylindrical configuration having a proximal end section and a distal end section, and a middle section between the proximal end section and the distal end section, the lattice being movable from a crimped state to an expanded state, the lattice having a plurality of adjacent hoops;
   a plurality of bridges connecting adjacent hoops;
   a plurality of extensions on the lattice; the extensions comprise a center arm terminating in a bifurcation;
   each of the hoops and bridges defining a cell, the extensions having one end integrally formed with the lattice and another end extending into the cell; and
   the proximal end section and the distal end section of the lattice having at least one cell respectively and the middle section of the lattice having at least one cell, the at least one cell of the middle section having spacing between adjacent hoops that is greater than spacing between adjacent hoops of the at least one cell of the proximal end section and the distal end section respectively.

2. The stent according to claim 1, wherein the plurality of extensions are on the middle section of the lattice.

3. The stent according to claim 2, wherein the plurality of extensions are cantilevered projections from the bridges of the lattice.

4. The stent according to claim 3, wherein the plurality of extensions are movably deformable in a direction away from the lattice.

5. The stent according to claim 4, wherein at least some of the extensions are movably deformable in a direction away from the bridges.

6. The stent according to claim 4, wherein one or more of the extensions comprise one or more arms extending from the bifurcation.

7. The stent according to claim 6, wherein one or more of the extensions comprise a first arm and a second arm extending from the bifurcation.

8. The stent according to claim 7, wherein the first arm is at a length shorter than the length of the second arm.

9. The stent according to claim 4, further comprising a drug on one or more portions of the lattice.

10. The stent according to claim 9, further comprising a drug and polymer combination on one or more portions of the lattice.

11. The stent according to claim 10, wherein the drug comprises rapamycin.

12. The stent according to claim 10, wherein the drug comprises paclitaxel.

13. The stent according to claim 4, wherein the stent is made of metal alloy.

14. The stent according to claim 4, wherein the stent is made of a superelastic material.

15. The stent according to claim 4, wherein the stent is made of a superelastic alloy.

16. The stent according to claim 4, wherein the stent is made of a polymeric material.

17. The stent according to claim 4, wherein the stent is made of a biodegradable polymer.

18. The stent according to claim 2, wherein at least some of the extensions are located on at least some of the hoops and are movably deformable in a direction away from the hoops.

19. The stent according to claim 1, wherein the bifurcation is shaped to receive the apex of an adjacent bridge in a crimped state.

20. The stent according to claim 1, wherein a plurality of cells having spacing between adjacent hoops that is greater than spacing between adjacent hoops of the at least one cell of the proximal end section and the distal end section, extending circumferentially around the middle section.

* * * * *